(12) United States Patent
Braun et al.

(10) Patent No.: US 7,145,046 B2
(45) Date of Patent: Dec. 5, 2006

(54) PRODUCTION OF FLUORINE COMPOUNDS

(75) Inventors: Max Braun, Wedemark (DE); Carsten Brosch, Hannover (DE)

(73) Assignee: Solvay Fluor und Derivate GmbH, Hannover (DE)

( * ) Notice: Subject to any disclaimer, the term of this patent is extended or adjusted under 35 U.S.C. 154(b) by 601 days.

(21) Appl. No.: 10/632,103

(22) Filed: Aug. 1, 2003

(65) Prior Publication Data

US 2004/0097758 A1    May 20, 2004

Related U.S. Application Data

(63) Continuation of application No. PCT/DE02/00276, filed on Jan. 26, 2002.

(30) Foreign Application Priority Data

Feb. 2, 2001   (DE) ................. 101 04 663

(51) Int. Cl.
*C07C 17/20* (2006.01)
*C07C 17/02* (2006.01)
*C07C 17/04* (2006.01)
*C07C 17/08* (2006.01)
*C07C 17/087* (2006.01)

(52) U.S. Cl. .............. 570/165; 570/140; 570/141; 570/142; 570/143; 570/144; 570/145; 570/164; 570/175; 564/1.5

(58) Field of Classification Search .......... 570/142, 570/140, 141, 143, 144, 145, 165, 164, 175; 564/1.5
See application file for complete search history.

(56) References Cited

U.S. PATENT DOCUMENTS 5,391,811 A    2/1995   Boehm et al.

| 6,417,361 B1 | 7/2002 | Hayashi et al. ......... 544/334 |
| 6,521,199 B1 | 2/2003 | Braun et al. ............. 423/83 |
| 6,723,874 B1 | 4/2004 | Braun |

FOREIGN PATENT DOCUMENTS

| DE | 199 42 374 | 5/2000 |
| DE | 10104663 | 8/2002 |
| EP | 0 005 810 | 12/1979 |
| EP | 0 597 329 | 10/1993 |
| EP | 1 072 576 | 1/2001 |
| JP | 63-128086 | 5/1988 |
| WO | WO-9843933 A1 | 10/1998 |

OTHER PUBLICATIONS

XP-002199359, Abstract of JP 63 128086 A, "Jet Printing Inks", May 31, 1998.
International Search Report dated Jun. 4, 2002.
Franz, R., *Journal of Fluorine Chemistry.* 15 (1980) pp. 423-434 (Abstract XP 000617966).

*Primary Examiner*—Elvis O. Price
(74) *Attorney, Agent, or Firm*—Crowell & Moring LLP

(57) ABSTRACT

Inorganic and organic compounds containing fluorine can be produced, for example, from corresponding chlorine-containing compounds by chlorine/fluorine exchange using fluorinating agents. Monocyclic or bicyclic compounds containing at least two nitrogen atoms, at least one of which is incorporated into the ring system, can be used as catalysts or fluorinating agents for chlorine/fluorine exchange reactions to produce sulfurylchlorofluoride, sulfurylfluoride or a carboxylic acid fluoride. It is likewise possible to carry out HF addition to unsaturated carbon-carbon bonds or chlorine/fluorine exchange at carbon atoms. For example, monochloro or dichloro malonic acid esters can be converted to difluoro malonic acid esters. Work-up of the reaction mixture can be simplified by using suitable solvents which force the reaction mixture to exist in two phases.

20 Claims, No Drawings

PRODUCTION OF FLUORINE COMPOUNDS

CROSS REFERENCE TO RELATED APPLICATIONS

This application is a continuation of international patent application no. PCT/DE02/00276, filed Jan. 26, 2002, designating the United States of America, and published in German as WO 02/060838, the entire disclosure of which is incorporated herein by reference. Priority is claimed based on Federal Republic of Germany patent application no. DE 101 04 663.4, filed Feb. 2, 2001.

BACKGROUND OF THE INVENTION

This invention relates to a process for producing fluorine-substituted compounds from chlorine-substituted compounds by chlorine-fluorine exchange or by addition of HF to C—C multiple bonds.

Organic and inorganic fluorine compounds are extremely important in chemistry and technology. Inorganic acid fluorides, e.g., sulfuryl fluoride or sulfuryl chlorofluoride, are products for use per se as well as being intermediates. Sulfuryl chloride, for example, has been proposed as a catalyst for synthesis of fluorocarbon compounds. Sulfuryl chlorofluoride is an intermediate for synthesis of sulfuryl fluoride. Sulfuryl fluoride can be added onto unsaturated hydrocarbons, and the resulting sulfonyl fluoride can be used as a catalyst. Carbon compounds and hydrocarbon compounds containing fluorine have a variety of applications, e.g., as propellants for the production of plastics, as refrigerants or as solvents. Carboxylic acids and carboxylic acid derivatives (e.g., carboxylic acid esters or dicarboxylic acid esters) having a carbon-fluorine bond can in turn be used as such or as intermediates in chemical synthesis.

Trifluoroacetic acid esters can be used, for example, as solvents and as intermediates in the production of trifluoroethanol. α-Fluoro-β-dicarbonyl compounds are important intermediates, e.g., in the synthesis of α-fluoroacrylic acid esters, see European patent application no. EP 597,329. European patent application no. EP 597,329 and published German patent application no. DE 199 42 374 disclose the possibility of using HF adducts of amines as catalysts in fluorination reactions or as fluorination agents. European patent application no. EP 1,072,576 discloses HF adducts of fluorination agents and the use of ureas and phosphoric acid amides, optionally cyclic, as fluorination agents. Japanese Patent Application 63/128,086 discloses the hydrofluoride of 1,8-diazobicyclo[5.4.0]undec-7-ene as an ingredient of ink.

SUMMARY OF THE INVENTION

The object of the present invention is to provide novel HF adducts of nitrogen compounds having improved properties and their use in fluorination. These objects are achieved by the novel HF adducts and the method of use according to this invention.

The method according to this invention for synthesis of compounds containing fluorine from compounds containing halogen, preferably chlorine, by halogen-fluorine exchange or by addition of HF to C—C multiple bonds is performed in the presence of the HF adduct of a monocyclic or bicyclic amine having at least two nitrogen atoms, at least one nitrogen atom being incorporated into the ring system, as a catalyst or as a fluorination agent. Under normal conditions, gaseous or liquid compounds are preferably produced.

According to one embodiment, monocyclic compounds are used. These may be saturated or unsaturated five-membered ring compounds, six-membered ring compounds or seven-membered ring compounds. At least one nitrogen atom is incorporated into the ring. Another nitrogen atom may also be incorporated into the ring system. Alternatively or additionally, the ring may be substituted by one or more amino groups. Dialkylamino groups in which the alkyl groups may be the same or different and include one to four carbon atoms are preferred. The amino group may also be a saturated ring system, e.g., a piperidine group. Highly suitable representatives of monocyclic ring systems include dialkylaminopyridine, dialkylaminopiperidine and dialkylaminopiperazine.

According to another embodiment, the amine compounds are bicyclic compounds. Here again, one, two or more nitrogen atoms may be integrated into the ring system. These compounds likewise may have one or more amino group substituents. Again dialkylamino groups are preferred, where the alkyl groups may be the same or different and may have one to four carbon atoms, or together with the nitrogen atom, they may form a saturated ring system such as the piperidinyl group, for example.

Bicyclic amines, in particular 1,5-diazabicyclo[4.3.0]non-5-ene (DEN) and 1,8-diazabicyclo[5.4.0]undec-7-ene (DBU), are especially preferred.

It is clear from the foregoing that at least two nitrogen atoms in the usable compounds must have basic properties and, depending on the type of bonds, must be bonded to two or three carbon atoms.

The compounds mentioned above having at least two nitrogen atoms are used in the form of the HF adduct. They may either be synthesized in advance by reacting the amines with hydrogen fluoride, or as an alternative, they may also be synthesized in situ if hydrogen fluoride is introduced accordingly into the reaction mixture.

According to one embodiment, organic or inorganic acid fluorides are synthesized from the corresponding acid chlorides. Preferred acid fluorides include sulfuryl chlorofluoride and sulfuryl fluoride, both of which can be synthesized from sulfuryl chloride or a mixture of chlorine and sulfur dioxide. Alkyl and aryl fluorosulfonates can also be synthesized from the corresponding chlorosulfonates. Chlorophosgene can be fluorinated to fluorophosgene.

Carboxylic acid fluorides can be synthesized from carboxylic acid chlorides. Carboxylic acid fluorides or dicarboxylic acid fluorides are preferably synthesized from the corresponding carboxylic acid chlorides and/or dicarboxylic acid chlorides having a chain length with a total of up to 12 carbon atoms. Aliphatic and aromatic carboxylic acid fluorides can be synthesized in this way. They may also be substituted with halogen atoms, e.g., fluorine and/or chlorine atoms. Aliphatic acid fluorides having a total of 2 to 7 carbon atoms, in particular 2 to 4 carbon atoms, are preferably produced. Acetyl fluoride, difluoroacetyl fluoride, chlorodifluoroacetyl fluoride or trifluoroacetyl fluoride are preferably produced. In addition, propionyl fluoride and propionyl fluoride substituted with 1 to 5 fluorine atoms can also be readily produced.

The method according to this invention may also be used to synthesize fluorine-containing compounds having a C—F bond from chlorine-containing compounds having a C—Cl bond. Converting C(O)Cl groups [into] C(O)F groups has already been mentioned above. For example, chloroalkanes having 1 to 5 carbon atoms can be converted to alkanes having fluorine substituents and optionally also chlorine substituents.

This method is also highly suitable for chlorine-fluorine exchange on activated carbon atoms, e.g., on carbon atoms in the α-position to C(O) groups. For example, chlorine-substituted ketones or diketones, chlorine-substituted aliphatic carboxylic acid compounds or dicarboxylic acid compounds with a chlorine substituent on the carbon bridge can be fluorinated. Fluorine-containing carboxylic acid derivatives such as fluorinated carboxylic acid fluorides, carboxylic acid esters or carboxylic acid amides are preferably produced. It is also preferable to produce alkylene-bridged dicarboxylic acid derivatives or diketones having at least one fluorine atom substituent in the alkylene bridge, which is preferably one to two carbon atoms long. This may be performed by starting with the chlorine compounds or also the bromine compounds. This process can be used very well for synthesis of the compounds described in European patent application no. EP 597,329. These are compounds of formula (I)

A-C(O)—C(R)(F)—C(O)-A in which the two A moieties may be the same or different and each stands for alkyl, aryl, alkoxy, aryloxy or an amino group and R stands for hydrogen, fluorine, alkyl or aryl.

The starting material is a compound of formula (II)

A-C(O)C(XR')—C(O)-A wherein

X repesents chlorine, bromine or iodine,

A has the meaning given for formula (I) and

R' has the meaning given for R in formula (I), and in addition, it may also represent chlorine, bromine or iodine.

The reaction is advantageously carried out at temperatures of 20° C. to 100° C. If R' in the starting material of formula (II) is bromine or iodine, then an α,α-difluoro-β-dicarbonyl compound is obtained, i.e., a compound of formula (I) in which R represents fluorine.

In formulas (I) and (II), A may, for example, represent a linear or branched, substituted or unsubstituted alkyl, a substituted or unsubstituted aryl, a linear or branched, substituted or unsubstituted alkoxy, a substituted or unsubstituted aryloxy or a substituted or unsubstituted amino group of formulas (III) to (V)

$$NH^2, \quad (III)$$

$$NHR^1 \quad (IV)$$

and $$NR^2R^3 \quad (V)$$

in which $R^1$, $R^2$ and $R^3$ denote alkyl, preferably $C_2$ to $C_6$ alkyl, or aryl, preferably phenyl. $R^2$ and $R^3$ may be the same or different.

The substituents optionally present on the alkyl and alkoxy groups may be, for example, halogen atoms, preferably fluorine, chlorine and/or bromine, or nitro groups.

The substituents optionally present on the aryl and aryloxy groups may include, for example, $C_1$ to $C_6$ alkyl groups, preferably methyl or ethyl, halogen atoms, preferably fluorine, chlorine and/or bromine, or nitro groups.

When A stands for an alkyl or alkoxy, it preferably has one to six carbon atoms, in particular one to two carbon atoms, and when A stands for an aryl or aryloxy, it preferably stands for phenyl.

In formulas (I) and (II), R and R' may represent, e.g., hydrogen, a linear or branched, substituted or unsubstituted $C_1$ to $C_{12}$ alkyl or a substituted or unsubstituted phenyl. Alkyl group substituents may include, for example, halogen atoms or nitro groups, and Aryl group substituents may include, for example, $C_1$ to $C_6$ alkyl groups, halogen atoms or nitro groups. In formula (II), R' may also represent chlorine, bromine or iodine, in particular chlorine or bromine. R and R' preferably represent hydrogen, or R' represents chlorine and R represents fluorine.

In formula (II), X preferably stands for chlorine or bromine. Fluoromalonic acid dialkyl ester and difluoromalonic acid dialkyl ester are preferably produced. Alkyl here is $C_1$ to $C_4$. For example, 2,2-difluoropropioic acid and derivatives thereof, such as esters, e.g., $C_1$ to $C_4$ alkyl or aryl esters, can be produced from the corresponding 2,2-dichloropropionic acid compounds.

As already described in published German patent application no. DE 199 42 374, the hydrofluoride adduct may also be used as a fluorination agent. It should then be used in an amount such that, or the reaction is performed as long as, the hydrofluoride adduct is not dehydrofluorinated to the extent that HCl adducts are formed. Otherwise regeneration with hydrogen fluoride is recommended. As already described in published German patent application no. DE 199 42 374, it is also possible to use the hydrofluoride adduct as a catalyst. Then HF is introduced into the reaction as a fluorination agent. The amount of HF is advantageously at least 1 mole HF per gram-atom of chlorine to be exchanged. Spent HF adduct may be regenerated with HF.

A continuous process is possible because the hydrofluoride adduct functions as a catalyst here.

Another embodiment includes addition of HF onto nucleophilic or electrophilic C—C double bonds or triple bonds. The preferred starting materials are unsaturated aliphatic hydrocarbon compounds which may be substituted with one or more halogen atoms. Preferred compounds are those having a $C_2$ to $C_4$ chain. These are especially preferably substituted with at least one chlorine or fluorine atom. For example, HF may be added to hexafluoropropene to synthesize 1,1,1,2,3,3,3-heptafluoropropane, or it may be added to tetrafluoroethylene to produce pentafluoroethane.

The process according to this invention may preferably be performed without solvents. This may be advantageous because it simplifies workup and there is no fear of interactions such as side reactions with the solvent.

As an alternative, however, this process may also be performed so that a solvent which induces the formation of two liquid phases is added during, or preferably after, the reaction, such that one phase contains the solvent and the organic compound, and the other phase contains the amino-HF adduct, so that separation of organic compounds from their mixtures with amine-HF adducts is possible by a simple method. Of course, this process also functions to separate mixtures containing two or more organic compounds. This embodiment including phase formation will now be described further.

The mixtures of amine-HF adducts and organic compounds result, e.g., from fluorination reactions when hydrogen fluoride is supplied during the fluorination reaction and/or the amine-HF adduct is not utilized as a fluorination reaction to such an extent that after the reaction, there is no longer any amine-HF adduct present, but instead there is amine-HCl adduct, when it is a chlorine-fluorine exchange reaction. Corresponding procedures are described, for example, in published German patent application no. DE 199 42 374 and in German patent application DE 101 04 663.4, published subsequent to the priority date of this application.

The process with the formation of two phases is preferably used for separating organic compounds having at least one fluorine atom as a substituent. For example, it is possible to separate hydrocarbons, cycloaliphatic hydrocarbons, aromatic hydrocarbons, esters, thioesters or ketones that are substituted with at least one fluorine atom.

The process of the invention is particularly advantageous when used for organic compounds, which cannot be separated well or at all by conventional methods such as distillation directly from the mixture with amine-HF adducts or by aqueous work-up. These include, for example, compounds with a boiling point higher than 50° C. or heat-labile compounds which cannot withstand temperatures above 50° C., for example, without decomposing. However, this process is advantageous in any case because according to this invention the amine-HF adduct is not hydrolyzed during work-up.

The invention also relates to new hydrofluoride adducts of 1,5-diazabicyclo[4.3.0]non-5-ene (DBN) and 1,8-diazabicyclo[5.4.0]undec-7-ene (DBU), in the case of DBU with the proviso that the molar ratio of HF to amine is greater than 1:1. They preferably have the formulas:

DBN.(HF)$_x$, where x is 1 or 1<x≦9 and

DBU.(HF)$_y$, where 1<y≦9.

The invention also relates to HF adducts of N-dialkylamino-pyridine, where alkyl stands for $C_1$ to $C_4$, in particular adducts wherein the molar ratio of HF to amine is greater than 1:1, preferably equal to or less than 9, most especially HF adducts in which alkyl is methyl.

The process according to this invention makes it possible to perform the fluorine-chlorine exchange in high yields, especially in the case of diketones and diesters.

The following examples are presented to further illustrate the present invention without restricting its scope in any way.

EXAMPLES 1 THROUGH 6

Chlorine-fluorine Exchange on Diesters

General Reaction Equation:

CH$_3$—CH$_2$—COO—CHCl—COO—CH$_2$—CH$_3$+ amine.HF→CH$_3$—CH$_2$—COO—CHF—COO—CH$_2$—CH$_3$+amine.HCl Fluorination experiments with DBU and DBN-HF/amine complexes in the absence of a solvent:

Example 1

Reactants:

| 0.15 mol 2-chloromalonic acid diethyl ester | 29.3 g |
| 0.3 mol 1,5-diazabicyclo[4.3.0]non-5-ene · 1.73 HF | 54.5 g |

Set-up and Procedure:
The amine complex was placed in a 100 ml PFA flask equipped with a reflux condenser (water cooling), then the chloromalonic acid diethyl ester was added and the mixture was heated at 80° C. in an oil bath while stirring. After 1, 3, 6 and 12 hours, samples were taken from the solution. The samples were hydrolyzed, dried with sodium sulfate and used for GC analysis. After 12 hours, 91.23% of the educt had been converted to fluoromalonic acid diethyl ester. The selectivity was quantitative.

Example 2

Reactants:

| 0.15 mol 2-chloromalonic acid diethyl ester | 29.3 g |
| 0.3 mol 1,8-diazabicyclo[5.4.0]undec-7-ene · 1.37 HF | 56.5 g |

Set-up and Procedure:
The amine complex was placed in a 100 ml PFA flask equipped with a reflux condenser (water cooling), then the chloromalonic acid diethyl ester was added and the mixture was heated in an oil bath at 80° C. while stirring. After 1, 3, 6, 12, 18 and 24 hours, samples were taken from the solution and were hydrolyzed, dried with sodium sulfate and used for GC analysis. After 24 hours, 72.5% of the educt had reacted to yield fluoromalonic acid diethyl ester. The selectivity was quantitative.

Example 3

Reactants:

| 0.10 mol 2-chloromalonic acid diethyl ester | 19.5 g |
| 0.05 mol 1,5-diazabicyclo[4.3.0]non-5-ene · 2.93 HF | 8.8 g |

Set-up and Procedure:
The amine complex was placed in a 100 ml PFA flask equipped with a reflux condenser (water cooling), then the chloromalonic acid diethyl ester was added and the mixture was heated in an oil bath at 80° C. while stirring. During the reaction, the solution became darker, turning from orange to dark red. After 1, 3, 6, 12 and 18 hours, samples of the solution were taken, hydrolyzed, dried with sodium sulfate and used for GC analysis. After 18 hours, 21.8% of the educt had reacted to yield fluoromalonic acid diethyl ester with a quantitative selectivity.

Example 4

Reactants:

| 0.10 mol 2-chloromalonic acid diethyl ester | 19.5 g |
| 0.05 mol 1,8-diazabicyclo[5.4.0]undec-7-ene · 3.09 HF | 10.7 g |

Set-up and Procedure:
The amine complex was placed in a 100 ml PFA flask equipped with a reflux condenser (water cooling), then the chloromalonic acid diethyl ester was added and the mixture was heated in an oil bath at 80° C. while stirring. After 1, 3 and 6 hours, samples of the solution were taken, hydrolyzed, dried with sodium sulfate and used for GC analysis. After 6 hours, 4.1% of the educt had reacted to yield fluoromalonic acid diethyl ester.

Example 5:(Comparative Example) Without Solvent

Reactants:

| | |
|---|---|
| 0.23 mol 2-chloromalonic acid diethyl ester | 53.1 g |
| 0.16 mol trimethylamine · 2.72 HF | 24.6 g |

Set-up and Procedure:

The chloromalonic acid diethyl ester was placed in a 100 ml multinecked flask equipped with a reflux condenser (water cooling), then the triethylamine complex was added by drops while stirring. The solution was heated at 100° C. in the oil bath. After 3 and 6 hours, samples were taken from the solution, hydrolyzed, dried with sodium sulfate and used for GC analysis. After 6 hours, 3.3% of the educt had reacted to yield fluoromalonic acid diethyl ester.

Example 6

Comparative Experiment in the Presence of Solvent with Trimethylamine.HF Complex Reactants:
0.375 mol 2-chloromalonic acid diethyl ester 73.125 g
0.5 mol trimethylamine.2.72 HF
0.25 mol triethylamine
125 ml acetonitrile Set-up and Procedure:

The amine complex was placed in a 100 ml PFA flask equipped with a reflux condenser (water cooling), and the acetonitrile was added. Then the chloromalonic acid diethyl ester was added and the mixture was heated in an oil bath at 80° C. while stirring. After 1, 3, 6, 12, 18 and 24 hours, samples of the solution were taken, hydrolyzed, dried with sodium sulfate and used for GC analysis. After 24 hours, 66.02% of the educt had reacted to yield fluoromalonic acid diethyl ester.

EXAMPLES 7 THROUGH 11

Synthesis of Acid Fluorides:

Set-up and Procedure: (Applicable to All Examples for Synthesis of Acid Fluorides)

The amine complex was placed in a 100 ml PFA flask with a reflux condenser and a dropping funnel. The reflux condenser was supplied with cold brine at −30° C. through a cryomat. To collect the reaction product, a steel cylinder (volume approx. 300 ml) having an immersion tube and a gas outlet was connected downstream from the condenser and was temperature controlled to −78° C. in a Dewar vessel with CO/methanol. At room temperature, $SO_2Cl_2$ was introduced into the oily light yellow solution slowly and with vigorous agitation. A short time after onset of the introduction, the evolution of gas was observed. After the end of the dropwise addition, an oil bath at 100° C. was placed beneath the flask and temperature controlled for one hour with cooling and one hour without cooling to completely expel the resulting $SO_2F_2$.

Example 7

Reactants:

| | |
|---|---|
| 0.20 mol sulfuryl chloride $SO_2Cl_2$ | 26.99 g |
| 0.24 mol 1,5-diazabicyclo[4.3.0]non-5-ene · 2.67 HF | 42.50 g |

Analysis:

After performing the general experimental procedure described above, thus 57.70% $SO_2F_2$ and 35.27% $SO_2FCl$, based on the quantity of educt used, were isolated.

Example 8

Reactants:

| | |
|---|---|
| 0.20 mol sulfuryl chloride $SO_2Cl_2$ | 26.99 g |
| 0.127 mol 1,5-diazabicyclo[4.3.0]non-5-ene · 7.19 HF | 42.50 g |

Analysis:

After performing the general experimental procedure described above, thus 90.65% $SO_2F_2$ and 0.34% $SO_2FCl$, based on the quantity of educt used, were isolated.

Example 9

Reactants:

| | |
|---|---|
| 0.20 mol sulfuryl chloride $SO_2Cl_2$ | 26.99 g |
| 0.253 mol 1,8-diazabicyclo[5.4.0]undec-7-ene · 5.58 HF | 40.90 g |

Analysis:

After performing the general experimental procedure described above, thus 0.04% $SO_2F_2$ and 69.87% $SO_2FCl$, based on the quantity of educt used, were isolated.

Example 10:(Comparative Example)

Reactants:

| | |
|---|---|
| 0.20 mol sulfuryl chloride $SO_2Cl_2$ | 26.99 g |
| 0.21 mol pyridine · 2.93 HF | 28.50 g |

Analysis:

After performing the general experimental procedure described above, thus 5.03% $SO_2F_2$ and 28.12% $SO_2FCl$, based on the quantity of educt used, were isolated.

Example 11

Reactants:

| | |
|---|---|
| 0.15 mol sulfuryl chloride SO$_2$Cl$_2$ | 20.25 g |
| 0.16 mol 4-dimethylaminopyridine · 2.93 HF | 28.90 g |

Analysis:

After performing the general experimental procedure described above, thus 16.40% SO$_2$F$_2$ and 21.76% SO$_2$FCl, based on the quantity of educt used, were isolated.

Example 12

Synthesis of Monofluoromalonic Acid Diethyl Ester and Extraction with Trifluoroacetic Acid Ethyl Ester

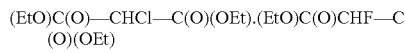

0.1 mol 2-chloromalonic acid diethyl ester was reacted with 0.2 mol 1,5-diazabicyclo[4.3.0]non-5-ene.1.4 HF at 80° C. for a period of 6 hours. After cooling, trifluoroacetic acid ethyl ester was added to the reaction mixture, and two phases developed. The phase containing the product and the solvent was separated, and the trifluoroacetic acid ethyl ester was distilled off to isolate the product. Phase separation was observed in the range from 25 mol % to 70 mol %.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A process for producing a fluorine-containing compound from a halogen-containing starting material, said process comprising effecting halogen-fluorine exchange or addition of HF to a C—C multiple bond in the presence of a catalyst or fluorination agent comprising an HF adduct of a monocyclic or bicyclic amine containing at least two nitrogen atoms, wherein at least one nitrogen atom is incorporated into the ring system.

2. A process according to claim 1, wherein said halogen-containing starting material is a chlorine-containing compound.

3. A process according to claim 1, wherein the HF adduct is an adduct of a monocyclic or bicyclic compound containing just two nitrogen atoms.

4. A process according to claim 1, wherein the monocyclic or bicyclic amine is selected from the group consisting of amino-substituted pyridines and bicyclic amines.

5. A process according to claim 4, wherein the monocyclic or bicyclic amine is selected from the group consisting of diazabicyclononane, diazabicycloundecane and dialkylaminopyridine.

6. A process according to claim 1, wherein the halogen containing starting material is an organic or inorganic acid chloride, and a corresponding acid fluoride is produced.

7. A process according to claim 6, wherein sulfuryl chlorofluoride or sulfuryl fluoride is produced.

8. A process according to claim 1, wherein the starting material is a compound containing chlorine and having a C—Cl bond, and a compound containing fluorine and having a C—F bond is produced.

9. A process according to claim 8, wherein a carbon or hydrocarbon compound containing fluorine is produced.

10. A process according to claim 8, wherein a fluorine-containing carboxylic acid derivative is produced.

11. A process according to claim 10, wherein the fluorine-containing carboxylic acid derivative is a carboxylic acid fluoride.

12. A process according to claim 10, wherein an alkylene-bridged dicarboxylic acid derivative substituted in the alkylene bridge by at least one fluorine atom is produced.

13. A process according to claim 12, wherein a monofluoro or difluoro malonic acid ester is produced.

14. A process according to claim 1, wherein the HF adduct of the monocyclic or bicyclic compound is used as a catalyst, and hydrogen fluoride is used as a fluorination agent.

15. A process according to claim 1, further comprising reconditioning spent HF adducts of the monocyclic or bicyclic compound using hydrogen fluoride.

16. A process according to claim 1, wherein at least one organic product compound having at least one fluorine atom substituent is produced, thereby resulting in a mixture of amine-HF adduct and fluorine-substituted product compound, said method further comprising adding a solvent to said mixture which causes two liquid phases to form, wherein one of the two phases contains the solvent and the at least one organic product compound, and the other phase contains the amine-HF adduct.

17. An HF adduct of an amine selected from the group consisting of 1,5-diazabicyclo[4.3.0]non-5-ene; N,N-di(C$_1$–C$_4$)alkylaminopyridine, and 1,8-diazabicyclo[5.4.0]undec-7-ene, wherein the molar ratio of HF to the amine is equal to 1 or greater than 1:1.

18. An adduct according to claim 17, wherein the molar ratio of HF to the amine is greater than 1:1.

19. An adduct according to claim 18, wherein the molar ration of HF to the amine is less than or equal to 9.

20. An adduct according to claim 17, wherein the amine is N,N-dimethylaminopyridine.

* * * * *